United States Patent [19]

Yokota et al.

[11] 4,048,307
[45] Sept. 13, 1977

[54] CYCLIC ADENOSINE MONOPHOSPHATE 8-SUBSTITUTED DERIVATIVES

[75] Inventors: Takeshi Yokota, Funabashi; Nobuyuki Suzuki, Hyuga; Tsuneo Sowa, Nobeoka; Yasuharu Sasaki, Nobeoka; Yasutaka Ono, Nobeoka, all of Japan

[73] Assignee: Asahi Kasei Kogyo Kabushiki Kaisha, Osaka, Japan

[21] Appl. No.: 616,356

[22] Filed: Sept. 24, 1975

[30] Foreign Application Priority Data

Dec. 26, 1974 Japan .................................. 49-3185
Dec. 27, 1974 Japan .............................. 49-148935

[51] Int. Cl.² .................... A61K 31/70; C07H 19/20
[52] U.S. Cl. .................................... 424/180; 536/27; 536/28
[58] Field of Search ................. 260/211.5 R; 536/27; 424/180

[56] References Cited

U.S. PATENT DOCUMENTS

| | | | |
|---|---|---|---|
| 3,712,885 | 1/1973 | Weimann et al. | 260/211.5 R |
| 3,752,805 | 8/1973 | Maguire et al. | 260/211.5 R |
| 3,872,098 | 3/1975 | Jones et al. | 260/211.5 R |

OTHER PUBLICATIONS

Boswell et al., Reprint from the Journ. of Heterocyclic Chem. 12, pp. 1-9, 1975.

*Primary Examiner*—Johnnie R. Brown
*Attorney, Agent, or Firm*—Burgess, Dinklage & Sprung

[57] ABSTRACT

Novel cyclic adenosine monophosphate derivatives represented by the following general formula:

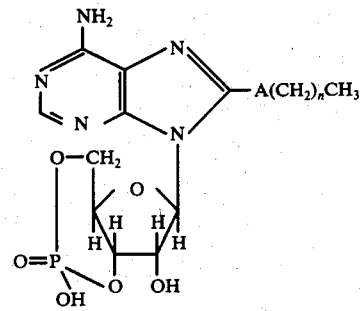

wherein A stands for —S— or —NH— and $n$ is an integer of from 2 to 12, are superior to known cyclic adenosine derivatives in biological and pharmacological activities, especially PDE-inhibiting activity and membrane permeability. Accordingly, these derivatives are very effective for remedying and controlling diseases caused by disorder of the intracellular cyclic adenosine monophosphate level, such as asthma and scabies. These derivaives can readily be synthesized by reacting an 8-halogeno cyclic adenosine monophosphate of the following general formula

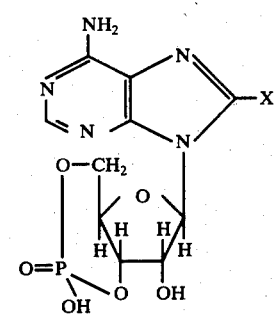

wherein X is a halogen atom such as bromine, with an alkali metal salt of a linear alkylmercaptan having 3 to 13 carbon atoms in the alkyl group or a linear alkylamine having 3 to 13 carbon atoms in the alkyl group.

37 Claims, No Drawings

CYCLIC ADENOSINE MONOPHOSPHATE 8-SUBSTITUTED DERIVATIVES

This invention relates to novel cyclic adenosine monophosphates having excellent biological and pharmacological activities and to processes for the preparation thereof. More particularly, the invention relates to novel 8-substituted cyclic adenosine derivatives represented by the following general formula and non-toxic salts thereof:

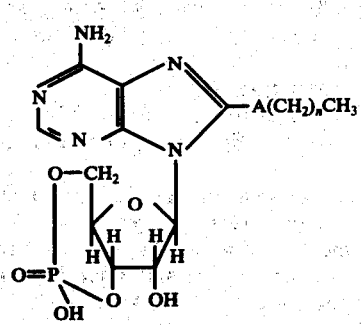

(I)

wherein A stands for a —S— or —NH— and $n$ is an integer of from 2 to 12,
and to processes for the preparation thereof.

In 1957, Sutherland et al found that when epinephrine and glucagon act on liver cells of higher animals, a low-molecular-weight nucleotide activating kinases is formed. Afterwards, this substance was identified as adenosine 3',5' cyclic-monophosphate (hereinafter referred to as "c-AMP"). The c-AMP is now designated as an intracellular second messenger of activities of hormones in higher animals. More specifically, when a certain hormone is bound to a hormone receptor of a target cell, an adenylate cyclase is activated to elevate the level of c-AMP. With elevation of the c-AMP level, c-AMP dependent protein kinases are activated and a variety of biological reactions are made vigorous. In some cases, unmasking of nucleohistons is stimulated and formation of various enzymes (proteins) is initiated. In another case, stored glucose or glycogen-phosphorylase is activated to accelerate glycogenolysis. A number of other biological reactions are influenced by the c-AMP level. Asthma can be mentioned as one of such biological reactions. The main cause of asthma is construed as reduction of the reactivity of the $\beta$-adrenegic receptor (one of the hormone receptors) of smooth muscles of respirators. The steroid enhances the reactivity of the $\beta$-adrenegic receptor and theophylline antagonizes and blocks a c-AMP decomposing enzyme (phosphodiesterase for c-AMP: hereinafter referred to as "PDE"). Both the chemicals have influences on elevation of the c-AMP level [A. Szentivanyi, J. Allergy, 42, 203–232 (1968)]. It is also construed that scabies, a skin disease, is caused by reduction of the c-AMP level. This is a disease caused by excessive proliferation of anomalous epithelial cells rich in glycogen, and this disease is characterized in that the function of the hormone receptor has already changed and it does not undergo actions of $\beta$-adregenic promotors, adenylate cyclase activators and NaF [J. J. Voorhees et al, Arch. Dermatol, 105, 695 (1972)]. There have heretofore been reported a considerable number of diseases caused by disorder of the c-AMP level.

The c-AMP is decomposed to 5'-adenoisine monophosphate by phosphodiesterase. In other words, intracellular levels of c-AMP are controlled by the difference of the activity between the synthesizing enzyme, adenylate cyclase and the decomposing enzyme, PDE. Biological activities of intracellular c-AMP are manifested through protein kinases. In view of these facts, we conducted research on 8-substituted c-AMP derivatives for the purpose of developing medicines for remedying and controlling diseases caused by abnormal levels of c-AMP. In short, 8-substituted derivative satisfying some or all of the following requirements have been synthesized:

1. To be stable under the activity of PDE.
2. To specifically inhibit PDE (to act as a competitive inhibitor to PDE).
3. To have an excellent membrane permeability.
4. To activate protein kinases.

While we were conducting chemical syntheses and biological tests, we found one novel biological fact, and based on this fact, we succeeded in synthesizing novel c-AMP derivatives having superior properties not possessed by known compounds.

Some 8-substituted c-AMP derivatives are known in the art. These known derivatives are classified as follows. In this classification, alkyl derivatives in which a linear alkyl group is bonded to the carbon atom at the 8-position through an amino or thio group are designated as alkylamino derivatives or alkylthio derivatives.

1. 8-Halogen-substituted derivatives (including Cl— and Br-derivatives)
2. 8-Alkylamino derivatives (including NH$_2$—, CH$_3$NH— and CH$_3$CH$_2$NH-derivatives)
3. 8-Alkylthio derivatives (including CH$_3$S— and CH$_3$CH$_2$S— derivatives)

As is seen from the above, in each of known 8-alkyl-substituted derivatives of c-AMP, the number of carbon atoms in the alkyl group is up to 2.

While we were synthesizing 8-alkyl-substituted c-AMP in which the number of carbon atoms in the alkyl group is increased, we found that novel derivatives in which the number of carbon atoms is 6 or more, namely CH$_3$(CH$_2$)$_5$NH— and CH$_3$(CH$_2$)$_5$S— derivatives and higher alkyl-substituted derivatives, have a much higher PDE-inhibiting activity than known derivatives. Further, it was found that novel derivatives in which the number of carbon atoms of the alkyl group is 10 or more, namely CH$_3$(CH$_2$)$_9$NH— and CH$_3$(CH$_2$)$_9$S—derivatives and higher alkyl-substituted derivatives, have a PDE-inhibiting activity and are excellent in living membrane permeability.

More specifically, novel c-AMP derivatives synthesized by us, which contain a linear alkyl group having 3 to 13 carbon atoms ($n$ in the general formula given hereinabove is from 2 to 12) as substituent bonded to the 8-position through an amino or thio group, act mainly as PDE-inhibitors in vivo and increase the intracellular level of c-AMP. Further, all of the novel substances now synthesized by us are not decomposed by c-AMP PDE but are very stable to the action of PDE. Data on main biochemical properties of these novel derivatives are illustrated in Table 1 given hereinafter.

For convenience, we divided these novel derivatives into the following three groups based on their activities:

1. Group I:
   8-CH$_3$(CH$_2$)$_n$NH-c-AMP (in which $n$ is from 2 to 4) and 8-CH$_3$(CH$_2$)$_n$S-c-AMP (in which $n$ is from 2 to 4).

2. Group II:
   8-$CH_3(CH_2)_n$NH-c-AMP (in which $n$ is from 5 to 8) and 8-$CH_3(CH_2)_n$S-c-AMP (in which $n$ is from 5 to 8).
3. Group III:
   8$CH_3(CH_2)_n$NH-c-AMP (in which $n$ is from 9 to 12) and 8-$CH_3(CH_2)_n$S-c-AMP (in which $n$ is from 9 to 12).

Derivatives of the group II having an alkyl group of 6 to 9 carbon atoms have a much higher PDE inhibiting activity than known c-AMP derivatives. Further, their inhibiting activity is much higher than that of known theophylline. Theophylline and its derivatives are used as anti-asthmatic agents. Novel c-AMP derivatives of the group II will take the place of these known anti-asthmatic agents.

Derivatives of the group III have a higher membrane permeability than known derivatives. From the results of experiments using protein kinases, it was confirmed that the derivatives of this group have no kinase activating property at all. In short, the derivatives of this group are PDE inhibitors excellent in the membrane permeability.

As pointed out hereinabove, scabies, which is a disease caused by reduction of the c-AMP level, is characterized in that functions of both the hormone receptor and adenylate cyclase have changed and their functions cannot be normalized (re-transformed), in general. As means for elevating the intracellular c-AMP level, there may be considered inhibition of PDE. In this connection, the derivatives of the group III have a high PDE inhibiting activity and are excellent in membrane permeability. Therefore, a sufficient curative effect can be expected by applying an ointment containing a derivative of group III to skins affected by scabies.

Biological tests made on novel c-AMP derivatives of this invention and results will now be illustrated.

1. Tests Using CHO-Ki Cultured Cells

In 1971, A. W. Hsie and T. T. Puck discovered that when $N^6,O^{2'}$-dibutyryl-c-AMP is added at a concentration of $10^{-3}$ mole/liter in medium containing cultured cells (CHO-Ki) derived from Chinese hamster, CHO-Ki is reversely transformed from the epitherial form to the fibroblast form (Proc. Nat. Acd. Sci. U.S., 68, 358–361). Afterwards, they clarified that $N^6$, $O^{2'}$-dibutyryl-c-AMP inhibits PDE to elevate the intracellular c-AMP level and activate protein kinases.

We utilized their test system and tested new derivatives as regards the following two properties:
1. Ability to elevate the c-AMP level in CHO-Ki cells.
2. Membrane permeability.

The tests were conducted in the following manner according to the modification of the method of Hsie and Puck:

1. In order to evaluate the ability to elevate the c-AMP level, new derivatives were added to the above-mentioned medium at a concentration of 1 millimole/liter of $10^{-1}$ millimole/liter and, after 24 hours, microscopic analysis was conducted. As controls, the medium of CHO-Ki cells free of any biological compound and the medium of CHO-Ki cells containing $10^{-3}$ mole/liter of $N^6$, $O^{2'}$-dibutyryl-c-AMP were similarly tested.

2. The membrane permeability was evaluated based on the reverse transformation. More specifically, new derivatives were added at a concentration of $10^{-3}$, $5 \times 10^{-2}$, $10^{-1}$, $2 \times 10^{-1}$, $5 \times 10^{-1}$ or 1 millimole/liter to the above-mentioned medium. After 16 and 30 hours, microscopic analysis was conducted, and the limiting reverse-transformable concentration (referred to as "L.R.C.") was determined and the membrane permeability was evaluated, based on the so determined L.R.C. value.

Results obtained at these tests are as shown in Tables 1 and 2.

Table 1

| New c-AMP Derivatives of This Invention (group) | c-AMP | | Known Substances N⁶,O²'-Dibutyryl-c-AMP [N⁶,O²'-(CH₃CH₂CH₂CO)₂-c-AMP] | | | 8-Bromo-c-AMP (8-Br-c-AMP) | | | 8-methylamino-c-AMP (8-CH₃NH-c-AMP) | | |
|---|---|---|---|---|---|---|---|---|---|---|---|
| | Stability to PDE* | Membrane Permeability*** | Stability to PDE* | PDE Inhibition** | Membrane Permeability*** | Stability to PDE* | PDE Inhibition** | Membrane Permeability*** | Stability to PDE* | PDE Inhibition** | Membrane Permeability*** |
| New Derivatives of Group I | ++ | + | + | + | − | + | + | ± | ± | ± | − |
| New Derivatives of Group II | ++ | + | + | ++ | ± | + | ++ | + | ± | ++ | ± |
| New Derivatives of Group III | ++ | ++ | + | + | ++ | + | + | ++ | ± | + | ++ |

Notes:
*$D_{II}$ fraction obtained by partial purification of phosdiesterase derived from the hog brain was used as a standard enzyme, and the stability to PDE was evaluated by the decomposition ratio at a concentration of 1 millimole/liter.
**PDE inhibition was evaluated based on the relative inhibition observed when the sample compound was added at the same molar concentration as that of the substrate (1 millimole/liter) and the inhibition constant (ki) calculated according to the enzymological method (Lineweaver-Burk plot).
***The membrane permeability was determined based on the minimum concentration causing the re-transformation of cultured CHO-Ki cells. (The re-transformation of CHO-Ki is caused by elevation of the c-AMP level.)

Symbols appearing in Table 1 indicate results of comparison of the foregoing properties between the new derivatives of this invention and the known compounds, and they have the following meaning:
++: The new derivative of this invention is much superior to the known compound.
+: The new derivative of this invention is superior to the known compound.
±: There is no substantial difference of the property between the new derivative of this invention and the known compound.
−: The known compound is superior to the new derivative of this invention.

Table 2
Reverse Transformation of Cultured Cells (CHO-Ki) by Novel 8-Substituted c-AMP Derivatives

| Compound | Reverse Transformation at $10^{-4}$ mole/liter | Reverse Transformation at $10^{-3}$ mole/liter | L.R.C. ($10^{-3}$ mole/liter) |
|---|---|---|---|
| 1. c-AMP | C | C | — |
| 2. $N^6,O^{2'}(CH_3CH_2CH_2CO)_2$-c-AMP | C | A | 0.2 ~ 0.4 |
| 3. 8-Br-c-AMP | C | A | 0.2 ~ |
| 4. 8-$CH_3$NH-c-AMP | C | A | 0.5 ~ |
| 5. 8-$CH_3(CH_2)_2$NH-c-AMP | C | C | — |
| 6. 8-$CH_3(CH_2)_3$NH | C | A | 0.3 ~ |
| 7. 8-$CH_3(CH_2)_4$NH | C | C | — |
| 8. 8-$CH_3(CH_2)_5$NH | C | C | — |
| 9. 8-$CH_3(CH_2)_6$NH | C | C | — |
| 10. 8-$CH_3(CH_2)_7$NH | C | C | — |
| 11. 8-$CH_3(CH_2)_8$NH | C | C | — |
| 12. 8-$CH_3(CH_2)_9$NH | A | C(Toxic) | 0.08 ~ |
| 13. 8-$CH_3(CH_2)_{10}$NH | A | C(Toxic) | 0.05 ~ |
| 14. 8-$CH_3(CH_2)_{11}$NH | A | C(Toxic) | 0.07 ~ |
| 15. 8-$CH_3(CH_2)_{12}$NH | A | C(Toxic) | 0.09 ~ |
| 16. 8-$CH_3(CH_2)_2$S-c-AMP | C | A | 0.4 ~ |
| 17. 8-$CH_3(CH_2)_3$S | C | A | 0.4 ~ |
| 18. 8-$CH_3(CH_2)_4$S | C | A | 0.4 |
| 19. 8-$CH_3(CH_2)_5$S | C | A | 0.3 |
| 20. 8-$CH_3(CH_2)_6$S | C | A | 0.3 |
| 23. 8-$CH_3(CH_2)_7$S | A | C(Toxic) | 0.02 |
| 24. 8-$CH_3(CH_2)_8$S | A | C(Toxic) | 0.01 |
| 25. 8-$CH_3(CH_2)_9$S | A | C(Toxic) | <0.005 |
| 26. 8-$CH_3(CH_2)_{10}$S | A | C(Toxic) | <0.005 |
| 27. 8-$CH_3(CH_2)_{11}$S | A | C(Toxic) | <0.005 |

Notes:
A: highest activity in reverse transformation
B: capable of reverse transformation
C: no detectable reverse transformation From the above test results, it will readily be understood that in the new derivatives of this invention, when the number of carbon atoms in the alkyl group is 9 or more, the L.R.C. value decreases regardless of whether the alkyl group is bonded to the 8-position through the amino group or the thio group. The reason is believed to be that as the number of methylene groups increases in the alkyl group (namely, as n in the above general formula is greater), the hydrophobic property is enhanced and permeation through cell membranes is facilitated. By other experiments, it was confirmed that the new derivatives having 8 or more carbon atoms in the alkyl group no longer act as c-AMP to protein kinases. Namely, in the case of these derivatives, the reverse transformation of CHO-Ki (elevation of the intracellular c-AMP level) is caused exclusively by PDE inhibition.

2. Tests Using Hog Brain Phosphodiesterase (PDE)

In general, c-AMP is decomposed to 5'-AMP by PDE present in cells and it loses the activity or function of c-AMP. It is because of this decomposition by PDE that c-AMP is often ineffective in various experiments and clincial trials. Accordingly, in order for c-AMP derivatives to be sufficiently effective, it is important first of all that they should have a high stability against the action of PDE. On the other hand, they should also have a high inhibiting activity to the enzyme, i.e., PDE. Accordingly, we selected as a standard enzyme PDE extracted from the hog brain cortex and partially purified according to the method of Teo, Wang et al. This standard enzyme did not contain other contaminant eseterase (5'-nucleotidase).

The enzyme purification was conducted by ammonium sulfate fractionation and passage through DEAE cellulose column according to the modification of the method of T. S. Teo, T. T. Wang et al. (J. Biol. Chemi. 248, 585). The reaction mixture (10 ml) comprised 40 millimoles of tris-HCl (pH = 8.0), 3 millimoles of $MgCl_2$, 0.3–4.0 millimoles of c-AMP, 0.5 or 1.0 millimole of the c-AMP derivative and 82 μg, as the protein, of the enzyme. Reaction and analysis were carried out as taught by Bucher and Sutherland [J. Biol. Chemi., 237, 1244 (1962)].

The test results are as shown in Table 3.

Table 3
Inhibitory Effects of 8-Substituted c-AMP Derivatives on Hydrolysis of c-AMP by Hog Brain Phosphodiesterase

| Compound | Inhibition I Concentration (millimole/liter) in Reaction Mixture c-AMP | Inhibition I Concentration (millimole/liter) in Reaction Mixture Derivative | Inhibition I Relative Inhibition* (%) | Inhibition II Inhibition Constant (Ki)** (mM) |
|---|---|---|---|---|
| c-AMP | 1.0 | — | 0 | — |
| 8-Br-c-AMP | 1.0 | 1.0 | 38.9 | 0.47 |
| 8-$CH_3$NH-c-AMP | 1.0 | 1.0 | 47.6 | 0.21 |
| 8-$CH_3(CH_2)_2$NH-c-AMP | 1.0 | 1.0 | 51.1 | 0.23 |
| 8-$CH_3(CH_2)_3$NH-c-AMP | 1.0 | 1.0 | 55.6 | 0.12 |
| 8-$CH_3(CH_2)_4$NH-c-AMP | 1.0 | 1.0 | 62.3 | 0.072 |
| 8-$CH_3(CH_2)_5$NH-c-AMP | 1.0 | 1.0 | 76.1 | 0.058 |
| 8-$CH_3(CH_2)_6$NH-c-AMP | 1.0 | 1.0 | 78.2 | 0.026 |
| 8-$CH_3(CH_2)_7$NH-c-AMP | 1.0 | 0.5 | 80.0 | 0.0093 |
| 8-$CH_3(CH_2)_8$NH-c-AMP | 1.0 | 0.5 | 71.3 | 0.027 |
| 8-$CH_3(CH_2)_9$NH-a-AMP | 1.0 | 0.5 | 67.6 | 0.082 |
| 8-$CH_3(CH_2)_{10}$NH-c-AMP | 1.0 | 0.5 | 51.4 | 0.17 |
| 8-$CH_3(CH_2)_{11}$NH-c-AMP | 1.0 | 0.5 | 18.3 | 0.66 |
| 8-$CH_3(CH_2)_{12}$NH-c-AMP | 1.0 | 0.5 | 11.3 | 0.84 |
| 8-$CH_3(CH_2)_2$S-c-AMP | 1.0 | 1.0 | 60.1 | 0.078 |
| 8-$CH_3(CH_2)_3$S-c-AMP | 1.0 | 1.0 | 64.3 | 0.074 |
| 8-$CH_3(CH_2)_4$S-c-AMP | 1.0 | 1.0 | 76.7 | 0.040 |
| 8-$CH_3(CH_2)_5$S-c-AMP | 1.0 | 1.0 | 92.4 | 0.019 |
| 8-$CH_3(CH_2)_6$S-c-AMP | 1.0 | 0.5 | 90.4 | 0.0095 |
| 8-$CH_3(CH_2)_7$S-c-AMP | 1.0 | 1.0 | 95.0 | 0.016 |
| 8-$CH_3(CH_2)_8$S-c-AMP | 1.0 | 0.5 | 74.9 | 0.031 |
| 8-$CH_3(CH_2)_9$S-c-AMP | 1.0 | 0.5 | 68.2 | 0.046 |
| 8-$CH_3(CH_2)_{10}$S-c-AMP | 1.0 | 1.0 | 39.1 | 0.088 |
| 8-$CH_3(CH_2)_{11}$S-c-AMP | 1.0 | 1.0 | 26.4 | 0.14 |

Notes:
*: The values were calculated according the following equation: $100 \times (1 - a/b)$ in which a denotes the ratio of hydrolysis of c-AMP in the reaction mixture containing the inhibitor (the c-AMP derivative) and b denotes the ratio of hydrolysis of c-AMP in the reaction mixture containing no inhibitor.
**: Ki values were calculated from the slope of Lineweaver-Burk plot and the cross-point of Dixon plot.

None of the novel derivatives were decomposed by PDE, though $N^6,O^{2'}$-dibutyryl-c-AMP, 8-Br-c-AMP and 3-$NH_2$-c-AMP were decomposed by PDE. It was found that among the novel alkylamino-c-AMP derivatives of this invention, those that can be PDE inhibitors having a higher activity than known 8-$CH_3$NH-c-AMP and 8-$CH_3CH_2$NH-c-AMP are 8-$CH_3(CH_2)_n$NH-c-AMP derivatives in which n is from 5 to 9. It was also found that the PDE inhibiting activity of 8-$CH_3(CH_2)_n$NH-c-AMP derivatives in which n is 3 or 4 is slightly inferior or comparable to that of the known alkylamino derivatives. As regards the novel alkylthio derivatives of this invention, it was found that though the PDE inhibiting activity of 8-$CH_3(CH_2)_n$S-c-AMP derivatives in which n is 3 or 4 is comparable or slightly inferior to that of known 8-$CH_3$S-c-AMP and 8-$CH_3$-$CH_2$-S-c-AMP derivatives, the PDE inhibiting activity of 8-$CH_3(CH_2)_n$S-c-AMP in which n is from 5 to 8 is much higher than that of the known alkylthio derivatives. The inhibition constants of 8-$CH_3(CH_2)_7$NH-c-AMP and 8-$CH_3(CH_2)_6$S-c-AMP were found to be 9.3 mM and 9.5 mM, each of which is highest among the values of c-AMP derivatives heretofore synthesized.

In order to examine the inhibition mechanism of 8-substituted c-AMP derivatives, the Lineweaver-Burk plot was taken with respect to each derivative. Namely, the reaction was carried out at a substrate (c-AMP)

concentration of 0.3 to 4.0 millimole/liter and a derivative concentration of 0.5 millimole/liter. It was found that all of the new derivatives of this invention have an antagonistic inhibition mechanism (focusing on ν max). Thus, it was confirmed that all the novel derivatives now synthesized by us specifically inhibit the c-AMP decomposing enzyme, PDE.

More specifically, novel derivatives of the above-mentioned group II, namely 8-$CH_3(CH_2)_n$NH-c-AMP and 8-$CH_3(CH_2)_n$S-c-AMP in which $n$ is from 5 to 8, inhibit antagonistically PDE more highly than any of the known c-AMP derivatives. The new derivatives of the group II are PDE inhibitors, each of which has a higher inhibiting activity than that of theophylline or its derivative that is now used as an anti-asthmatic agent. Moreover, since the protein kinase-activating property is substantially lost in any of these derivatives of the group II, they act only as PDE inhibitors. Therefore, it is expected that they will take the place of theophylline as the principal anti-asthmatic agent.

Synthesis of the novel c-AMP derivatives of this invention will now be illustrated.

This invention is directed to a novel 8-substituted c-AMP represented by the following general formula (I) and its non-toxic inorganic and organic salts:

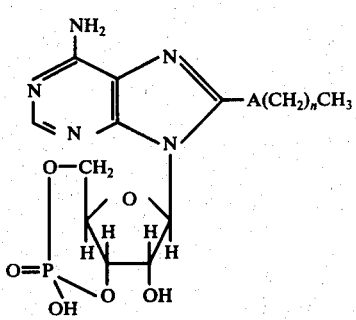

(I)

wherein A stands for —S— or —NH— and $n$ is n integer of from 2 to 12,
and to a process for the preparation thereof.

Novel 8-linear alkylmercapto cyclic AMP derivatives of formula (I) in which A stands for —S— in which $n$ is as defined above and their non-toxic inorganic and organic sals are synthesized by reacting 8-halogeno cyclic AMP derivative represented by the following general formula (II) or its organic or inorganic salt:

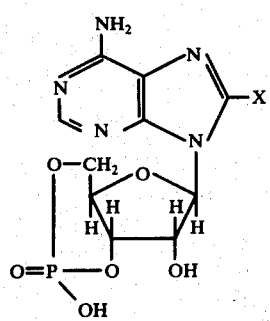

(II)

wherein X stands for a halogen atom such as bromine, with an alkali metal salt of a linear alkylmercaptan represented by the formula $CH_3(CH_2)_n$SH in which $n$ is an integer of from 2 to 12, in an alcoholic solvent.

8-Halogeno cyclic AMP derivatives to be used in this invention, for example, 8-bromo-c-AMP, can readily be synthesized by treating c-AMP with bromine in acetic acid buffer [M. Ikehara et al., Chem. Pharm. Bull., 17, 348 (1969)].

In this reaction, the 8-bromo-c-AMP may be used in either the free form or the form of an inorganic salt such as a sodium salt or a salt of an organic base such as triethylamine. An alcohol is used as the solvent. An alkali metal salt of the alkylmercaptan is formed according to a customary method, for example, by reacting the alkylmercaptan in an alcohol solvent with an alkali metal alcoholate such as methoxy sodium or t-butoxy potassium. The amount used of the alkali metal salt of the alkylmercaptan is at least one mole, preferably 2 to 10 moles, per mole of the 8-halogeno-c-AMP. Excessive use of the alkali metal salt of the alkylmercaptan is not preferred from the economical viewpoint and is disadvantageous in that the post treatment becomes troublesome. The reaction is carried out at the boiling point of the solvent used. The reaction time is greatly influenced by other reaction conditions, such as the amount used of the alkali metal salt of the alkyl mercaptan and the kind of the solvent used, but in general good results are obtained when the reaction is conducted for 1 to 5 hours. Too long a reaction time is not preferred because decomposition of the intended product is caused to occur. The product can readily be recovered in the form of a crystal of the free ester according to a customary method, for example, by concentrating the resulting reaction product liquid at 40° C. under reduced pressure, adding cool water to the concentrate to dissolve it in water and adding concentrated hydrochloric acid to the solution under cooling and agitation to adjust the pH to the acidic side.

The novel 8-linear alkylamino c-AMP of above formula (I) in which A stands for —NH— in which $n$ is as defined above, or its non-toxic inorganic or organic salt, can be synthesized by reacting a halogeno cyclic AMP of the abovementioned formula (II) or its organic or inorganic salt with a linear alkylamine represented by the formula $CH_3(CH_2)_n NH_2$ in which $n$ is an integer of from 2 to 12.

This reaction is carried out at 50° to 150° C. for 1 to 24 hours. Any solvent which does not interfere with the reaction may be used, but in view of the dissolving power, water or an alcohol is preferred as the reaction solvent. When the starting alkylamine has 10 or more carbon atoms, especially good results are obtained by the use of methoxyethanol. The amount used of the alkylamine is 1 to 20 moles per mole of the 8-halogeno-c-AMP. Use of great excess of the alkylamine is not preferred because the post treatment is troublesome and the preparation becomes costly though the reaction is not adversely influenced even by using the alkylamine in great excess. The reaction product can readily be isolated in the form of a crystal of the free ester according to a customary method, for example, by concentrating the reaction product liquid at 40° C. under reduced pressure, dissolving the residue in 0.5N aqueous ammonia, extracting the solution with ether to remove ether-soluble impurities such as excess alkylamine, adding concentrated hydrochloric acid to adjust the pH to the acidic side and, if desired, adding methanol, ethanol, acetone or the like.

Novel 8-substituted c-AMP derivatives of this invention are very stable in vivo and act in vivo mainly as antagonistic inhibitors for the c-AMP decomposing enzyme, PDE. Among these novel derivatives, those containing 5 to 10 carbon atoms in the alkyl group as the substituent have an especially high activity as the anatagonistic inhibitor for PDE. Further, since the protein kinase activating property is drastically reduced in these derivatives, they do not function as the c-AMP of the active type any more even if they are administered to the living body. In other words, in these derivatives, side effects by the direct elevation of the c-AMP level can be eliminated or moderated.

The compounds of the present invention are useful in the treatment of various disease states, including metabolic and endocrine disorders, by virtue of their ability to increase the levels of intracellular mediators of hormone effect. They demonstrate high biological activity and selectivity in action to different target tissues. They also show stability towards degenerative enzymes, i.e., cyclic phosphodiesterase. Thus, the compounds of the present invention are useful, for example, in the treatment of bronchial asthma, refractory congestive heart failure, diabetes mellitus, pseudohypoparathyroidism, obesity, some neoplastic manifestations, vasopressin resistant diabetes insipidus, and other disorders attributable to pituitary disfunction.

The present invention, in a second aspect, is directed to pharmaceutical compositions incorporating a compound of Formula (I) hereof as an essential active component in admixture with a pharmaceutically acceptable non-toxic carrier.

Useful pharmaceutical carriers for the preparation of the compositions hereof can be solids, liquids, or gases. Thus, the compositions can take the form of tablets, pills, capsules, powders, sustained release formulations, solutions, suspensions, elixirs, aerosols, and the like. The carriers can be selected from the various oils including those of petroleum, animal, vegetable, or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, and the like. Such compositions will, in any event, contain an effective amount of the active compound together with a suitable amount of carrier so as to prepare the proper dosage form for proper administration to the host.

The present invention also involves a method useful for the treatment of biological disorders which comprises administering an effective amount of a compound of Formula (I) hereof.

An amount of a compound hereof effective for the treatment of biological disorders in accordance herewith, can vary generally in the range of from about 1 mg. to about 100 mg. per kg. of host body weight administered one or more times daily. The active compound hereof can be administered in any suitable manner, parenteral or oral, and in any form suitable for the administration mode, isotonic solutions, suspensions, tablets, capsules, and the like (See, for example U.S. Patent No. 3,872,084).

The c-AMP derivatives of group II of this invention, especially 8-$CH_3(CH_2)_6$S-c-AMP and 8-$CH_3(CH_2)_7$NH-c-AMP, have a very high anti-asthmatic activity, and therefore, they take the place of theophylline or its derivative which is now used broadly as an anti-asthmatic agent.

The c-AMP derivatives of group III of this invention are antagonistic inhibitors for PDE which are superior to known c-AMP derivatives in respect to membrane permeability. When medicines containing these derivatives of this invention are applied to skin suffering from scabies or like skin diseases, these derivatives of group III are sufficiently absorbed to exhibit a high curative effect. Further, when these derivatives are administered to the living body, they are promptly absorbed in cells even at low concentrations and they exert their functions effectively.

The method for treatment of scabies, which is now considered most effective, involves inhibiting PDE and elevating the intracellular c-AMP level. In view of this fact, it will readily be understood that the novel c-AMP derivatives of this invention are very effective for the medicinal treatment of scabies.

Synthesis of the novel 8-substituted c-AMP derivatives of this invention will now be illustrated in more detail by reference to the following Examples.

EXAMPLE 1

In 60 ml of anhydrous methanol was dissolved 400 mg (18 millimoles) of metallic sodium, and 3.4 ml (24 millimoles) of n-hexylmercaptan was added to the solution. The mixture was agitated for about 30 minutes at room temperature. Then, 2.46 g (6 millimoles) of 8-bromo-c-AMP was added, and the mixture was heated and refluxed under agitation for 1 hour. The resulting reaction product liquid was concentrated at 40° C. and 60 ml of cold water was added to the residue. Then, the pH was adjusted to 6 under agitation by concentrated hydrochloric acid. The mixture was extracted two times with 100 ml of ether. The water layer was filtered, and the filtrate was cooled and concentrated hydrochloric acid was added under agitation to adjust the pH to 2. The mixture was cooled and agitated to effect crystallization. The precipitated crystal was recovered by filtration and was washed with small amounts of cold ethyl alcohol and ether to remove the smell of thiol. The crystal was then dried at room temperature under reduced pressure to obtain 2.16 g (81% yield) of a crystal of 8-n-hexylmercapto-c-AMP, properties of which were found to be as follows:

Decomposition Point: 225° C.

Ultraviolet Absorption Maximum: $\lambda_{max}^{pH_2}$ 285 m$\mu$, $\lambda_{max}^{pH_{13}}$ 282 m$\mu$, $\epsilon_{pH_2}^{285\ m\mu}$ 19,400, $E_{250}/E_{260}$ = 0.48 , $E_{280}/E_{260}$ = 2.36

Paper Chromatography[n-butanol:acetic acid:water = 4:1:5 (upper layer)]: Rf value = 0.65

Elementary Analysis Values as $C_{16}H_{24}N_5O_6SP$: Found: C = 43.24%, H = 5.95%, N = 15.57%, S = 7.02%, P = 6.73%. Calculated: C = 43.14%, H = 5.43%, N = 15.72%, S = 7.20%, P = 6.95%.

EXAMPLE 2

Procedures of Example 1 were repeated in the same manner except that 2.9 ml (24 millimoles) of n-amylmercaptan was used instead of 3.4 ml of n-hexylmercaptan, to obtain 2.22 g (85% yield) of a crystal of 8-n-amylmercapto-c-AMP, properties of which were found to be as follows:

Decomposition Point: 226° C.

Ultraviolet Absorption Maximum: $\lambda_{max}^{pH_2}$ 284 m$\mu$, $\lambda_{max}^{pH_{13}}$ 282 m$\mu$, $\epsilon_{pH_2}^{284\ m\mu}$ 19,600, $E_{250}/E_{260}$ = 0.45, $E_{280}/E_{260}$ = 2.46

Paper Chromatography[n-butanol:acetic acid:water = 4:1:5 (upper layer)]: Rf value = 0.65

Elementary Analysis Values as $C_{15}H_{22}N_5O_6SP$:
Found: C = 41.37%, H = 5.44%, N = 16.03%, S = 7.23%, P = 7.05%. Calculated: C = 41.76%, H = 5.14%, N = 16.23%, S = 7.43%, P = 7.18%.

EXAMPLE 3

Procedures of Example 1 were repeated in the same manner except that 2.6 ml (24 millimoles) of n-butylmercaptan was used instead of 3.4 ml of n-hexylmercaptan, to obtain 1.79 g (72% yield) of a crystal of 8-n-butylmercapto-c-AMP, properties of which were found to be as follows:
Decomposition Point: 224° C.
Ultraviolet Absorption Maximum: $\lambda_{max}^{pH_2}$ 284 m$\mu$, $\lambda_{max}^{pH_{13}}$ 282 m$\mu$, $\epsilon_{pH_2}^{284}$ m$\mu$ 20,100, $E_{250}/E_{260}$ = 0.44, $E_{280}/E_{260}$ = 2.52
Paper Chromatography [n-butanol:acetic acid:water = 4:1:5 upper layer)]: Rf value = 0.66
Elementary Analysis Values as $C_{14}H_{20}N_5O_6SP$:
Found: C = 40.02%, H = 5.33%, N = 15.50%, S = 7.48%, P = 7.24%. Calculated: C = 40.29%, H = 4.83%, N = 16.78%, S = 7.68%, P = 7.42%.

EXAMPLE 4

In 80 ml of ethyl alcohol was dissolved 400 mg (18 millimoles) of metallic sodium, and 4.2 ml (24 millimoles) of n-octylmercaptan was added to the solution. The mixture was agitated for 30 minutes at room temperature. Then, 2.46 g (6 millimoles) of 8-bromo-c-AMP was added and the mixture was heated and refluxed under agitation for 3 hours. In the same manner as described in Example 1, the resulting reaction product was post-treated to obtain 2.32 g (82% yield) of a crystal of 8-n-octylmercapto-c-AMP, properties of which were found to be as follows:
Decomposition Point: 223° C.
Ultraviolet Absorption Maximum: $\lambda_{max}^{pH_2}$ 285 m$\mu$, $\lambda_{max}^{pH_{13}}$ 282 m$\mu$, $\epsilon_{pH_2}^{285}$ m$\mu$ 18,400, $E_{250}/E_{260}$ = 0.48, $E_{280}/E_{260}$ = 2.70
Paper Chromatography [n-butanol:acetic acid:water = 4:1:5 (upper layer)]: Rf value = 0.65
Elementary Analysis Values as $C_{18}H_{28}N_5O_6SP$:
Found: C = 45.43%, H = 6.34%, N = 14.80%, S = 6.52%, P = 6.38% Calculated: C = 45.66%, H = 5.96%, N = 14.79%, S = 6.77% P = 6.54%

EXAMPLE 5

Procedures of Example 4 were repeated in the same manner except that 3.8 ml (24 millimoles) of n-heptylmercaptan was used instead of 4.2 ml of n-octylmarcaptan, to obatin 2.26 g (82% yield) of a crystal of 8-n-heptylmercapto-c-AMP, properties of which were found to be as a follows:
Decomposition Point: 228° C.
Ultraviolet Absorption Maximum: $\lambda_{max}^{pH_2}$ 285 m$\mu$, $\lambda_{max}^{pH_{13}}$ 282 m$\mu$, $\epsilon_{pH_2}^{285}$ m$\mu$ 19,300, $E_{250}/E_{260}$ = 0.47, $E_{280}/E_{260}$ = 2.45
Paper Chromatography [n-butanol:acetic acid:water = 4:1:5 (upper layer)]: Rf value = 0.65
Elementary Analysis Values as $C_{17}H_{24}N_5O_6SP$:
Found: C = 44.45%, H = 5.98%, N = 15.13%, S = 6.78%, P = 6.65%. Calculated: C = 44.44%, H = 5.70%, N = 15.24%, S = 6.98%, P = 6.74%.

EXAMPLE 6

In 100 ml of anhydrous t-butyl alcohol was dissolved 620 mg (20 millimoles) of metallic potassium under heating at 40° C. Then, 5.0 ml (24 millimoles) of n-decylmercaptan was added to the solution, and the mixture was agitated for about 20 minutes. Then, 2.46 g (6 millimoles) of 8-bromo-c-AMP was added to the mixture, and the mixture was heated and refluxed for 1 hour. The resulting reaction product was post-treated in the same manner as described in Example 1 to obtain 2.60 g (86% yield) of a crystal of 8-n-decylmercapto-c-AMP, properties of which were found to be as follows:
Decomposition Point: 227° C.
Ultraviolet Absorption Maximum: $\lambda_{max}^{pH_2}$ 285 m$\mu$, $\lambda_{max}^{pH_{13}}$ 282 m$\mu$, $\epsilon_{pH_2}^{285}$ m$\mu$ 17,800, $E_{250}/E_{260}$ = 0.52, $E_{280}/E_{260}$ = 2.69
Paper Chromatography [n-butanol:acetic acid:water = 4:1:5 (upper layer)]: Rf value = 0.75
Elementary Analysis Values as $C_{20}H_{32}N_5O_6SP$:
Found: C = 47.64%, H = 6.58%, N = 13.86%, S = 6.25%, P = 6.07%. Calculated: C = 47.90%, H = 6.43%, N = 13.96%, S = 6.39%, P = 6.18%.

EXAMPLE 7

Procedures of Example 6 were repeated in the same manner except that 5.7 ml (24 millimoles) of n-dodecylmercaptan was used instead of 5.0 ml of n-decylmercaptan, to obtain 2.70 g (85% yield) of a crystal of 8-n-dodecylmercapto-c-AMP, properties of which were found to be as follows:
Decomposition Point: 228° C.
Ultraviolet Absorption Maximum: $\lambda_{max}^{pH_2}$ 285 m$\mu$, $\lambda_{max}^{pH_{13}}$ 282 m$\mu$, $\epsilon_{pH_2}^{285}$ m$\mu$ 17,800, $E_{250}/E_{260}$ = 0.53, $E_{280}/E_{260}$ = 2.70
Paper Chromatography [n-butanol:acetic acid:water = 4:1:5 (upper layer)]: Rf value = 0.80
Elementary Analysis Values as $C_{22}H_{36}N_5O_6SP$:
Found: C = 49.60%, H = 6.85%, N = 13.02%, S = 5.95% P = 5.76%. Calculated: C = 49.90%, H = 6.85%, N = 13.22%, S = 6.05%, P = 5.89%.

EXAMPLE 8

Procedures of Example 4 were repeated in the same manner except that 2.18 ml (24 millimoles) of n-propylmercaptan was used instead of 4.2 ml of n-octylmercaptan, to obtain 1.94 g (80% yield) of a crystal of 8-n-propylmercapto-c-AMP, properties of which were found to be as follows:
Decomposition Point: 225° C.
Ultraviolet Absorption Maximum: $\lambda_{max}^{pH_2}$ 284 m$\mu$, $\lambda_{max}^{pH_{13}}$ 282 m$\mu$, $\epsilon_{pH_2}^{284}$ m$\mu$ 20,300, $E_{250}/E_{260}$ = 0.45, $E_{280}/E_{260}$ = 2.45
Paper Chromatography [n-butanol:acetic acid: water = 4:1:5 (upper layer)]: Rf value = 0.55
Elementary Analysis Values as $C_{13}H_{18}N_5O_6SP$:
Found: C = 38.78%, H = 4.86%, N = 17.08%, S = 7.80%, P = 7.55%, Calculated: C = 38.71%, H = 4.50%, N = 17.36%, S = 7.95%, P = 7.68%,

EXAMPLE 9

Procedures of Example 4 were repeated in the same manner except that 5.7 ml (30 millimoles) of n-nonylmercaptan was used instead of 4.2 ml of n-octylmercaptan, to obtain 2.49 g (85% yield) of a crystal of 8-n-nonylmercapto-c-AMP, properties of which were found to be as follows:
Decomposition Point: 225° C.
Ultraviolet Absorption Maximum: $\lambda_{max}^{pH_2}$ 285 m$\mu$, $\lambda_{max}^{pH_{13}}$ 282 m$\mu$, $\epsilon_{pH_2}^{285}$ m$\mu$ 18,200, $E_{250}/E_{260}$ = 0.49, $E_{280}/E_{260}$ = 2.70
Paper Chromatography [n-butanol:acetic acid:water = 4:1:5 (upper layer)]: Rf value = 0.68

Elementary Analysis Values: Found: C = 46.70%, H = 6.45%, N = 14.20%, S = 6.48%. P = 6.22%. Calculated: C = 46.81%, H = 6.20%, N = 14.37%, S = 6.57%, P = 6.35%.

EXAMPLE 10

Procedures of Example 1 were repeated in the same manner except that 5.4 ml (24 millimoles) of n-undecylmercaptan was used instead of 3.4 ml of n-hexylmercaptan, to obtain 2.32 g (75% yield) of a crystal of 8-n-undecylmercapto-c-AMP, properties of which were found to be as follows:

Decomposition Point: 227° C.

Ultraviolet Absorption Maximum: $\lambda_{max}^{pH2}$ 285 m$\mu$, $\lambda_{max}^{pH13}$ 282 m$\mu$, $\epsilon_{pH_2}^{285}$ m$\mu$ 17,800, $E_{250}/E_{260}$ Paper Chromatography [n-butanol:acetic acid:water = 4:1:5 (upper layer)]: Rf value = 0.75

Elementary Analysis Values as $C_{21}H_{34}N_5O_6SP$: Found: C = 48.83%, H = 6.80%, N = 13.67%, S = 6.09%, P = 6.12%. Calculated: C = 48.92%, H = 6.65%, N = 13.58%, S = 6.22% P = 6.01%.

EXAMPLE 11

To 20 ml of 2-methoxyethanol were added 820 mg (2 millimoles) of 8-bromo-c-AMP and 3.14 g (20 millimoles) of n-decylamine, and the mixture was heated and refluxed under agitation for 2 hours. The reaction mixture was thrown into 100 ml of 1N aqueous ammonia and extracted two times with 200 ml of ether. The water later was concentrated at 40° C. under reduced pressure until the volume was reduced to 10 ml. The concentrate was added dropwise under agitation to hydrochloric acid-containing methanol, the pH of which had been adjusted to 1.5 in advance, and agitation was continued overnight under cooling to effect crystallization. The precipitated crystal was recovered by filtration, washed with small amounts of cold water and cold ethanol and dried at room temperature under reduced pressure to obtain 805 mg (83% yield) of a crystal of 8-n-decylamino-c-AMP, properties of which were found to be as follows:

Decomposition Point: 226° C.

Ultraviolet Absorption Maximum: $\lambda_{max}^{pH2}$ 277 m$\mu$, $\lambda_{max}^{pH13}$ 277 m$\mu$, $\epsilon_{pH_2}^{277}$ m$\mu$ 12,700, $E_{250}/E_{260}$ = 0.74, $E_{280}/E_{260}$ = 1.34

Paper Chromatography [n-butanol:acetic acid:water = 4:1:5 (upper layer)]: Rf value = 0.83

Elementary Analysis Values as $C_{20}H_{33}N_6O_6P$: Found: C = 48.96%, H = 7.03%, N = 17.40%, P = 6.21%. Calculated: C = 49.58%, H = 6.86%, N = 17.35%, P = 6.39%.

EXAMPLE 12

Procedures of Example 11 were repeated in the same manner except that 3.43 g (20 millimoles) of n-undecylamine was used instead of 3.14 g of n-decylamine, to obtain 785 mg (79% yield) of a crystal of 8-n-undecylamino-c-AMP, properties of which were found to be as follows:

Decomposition Point: 225° C.

Ultraviolet Absorption Maximum: $\lambda_{max}^{pH2}$ 277 m$\mu$, $\lambda_{max}^{pH13}$ 277 m$\mu$, $\epsilon_{pH_2}^{277}$ m$\mu$ 12,300, $E_{250}/E_{260}$ = 0.87, $E_{280}/E_{260}$ = 1.31

Paper Chromatography [n-butanol:acetic acid:water = 4:1:5 (upper layer)]: Rf value = 0.86

Elementary Analysis Values as $C_{21}H_{35}N_6O_6P$: Found: C = 50.18%, H = 7.23%, N = 16.65%, P = 6.14%.

Calculated: C = 50.60%, H = 7.08%, N = 16.86%, P = 6.21%.

EXAMPLE 13

Procedures of Example 11 were repeated in the same manner except that 3.71 g (20 millimoles) of n-dodecylamine was used instead of 3.14 g of n-decylamine, to obtain 750 mg (73% yield) of a crystal of 8-n-dodecylamino-c-AMP, properties of which were found to be found as follows:

Decomposition Point: 227° C.

Ultraviolet Absorption Maximum: $\lambda_{max}^{pH2}$ 277 m$\mu$, $\lambda_{max}^{pH13}$ 277 m$\mu$, $\epsilon_{pH_2}^{277}$ m$\mu$ 12,100, $E_{250}/E_{260}$ = 0.88, $E_{280}/E_{260}$ = 1.30

Paper Chromatography [n-butanol:acetic acid:water = 4:1:5 (upper layer)]: Rf value = 0.86

Elementary Analysis Values as $C_{22}H_{37}N_6O_6P$: Found: C = 51.27%, H = 7.36%, N = 16.30%, P = 5.96%. Calculated: C = 51.55%, H = 7.28%, N = 16.40%, P = 6.04%.

EXAMPLE 14

Procedures of Example 11 were repeated in the same manner except that 3.99 g (20 millimoles) of n-tridecylamine was used instead of 3.14 g of n-decylamine, to obtain 650 mg (62% yield) of a crystal of 8-n-tridecylamino-c-AMP, properties of which were found to be as follows:

Decomposition Point: 234° C.

Ultraviolet Absorption Maximum: $\lambda_{max}^{pH2}$ 277 m$\mu$, $\lambda_{max}^{pH13}$ 277 m$\mu$, $\epsilon_{pH_2}^{277}$ m$\mu$ 12,000, $E_{250}/E_{260}$ = 0.87, $E_{280}/E_{260}$ = 1.35

Paper Chromatography [n-butanol:acetic acid:water = 4:1:5 (upper layer]: Rf value = 0.90

Elementary Analysis Values as $C_{23}H_{39}N_6O_6P$: Found: C = 51.30%, H = 7.32%, N = 16.04%, P = 5.75%. Calculated: C = 52.46%, H = 7.47%, N = 15.96%, P = 5.88%.

EXAMPLE 15

To 40 ml of n-butanol were added 820 mg (2 millimoles) of 8-bromo-c-AMP and 2.59 g (20 millimoles) of n-octylamine, and the mixture was refluxed (the inner temperature being 120° C.) under agitation for 3 hours. The reaction mixture was concentrated at 40° C. under reduced pressure, and 50 ml of 0.5N aqueous ammonia was added to the residue to dissolve it in the aqeous ammonia. The solution was extracted two times with 100 ml of ether, and the water layer was filtered. The pH of the filtrate was adjusted to 1.5 by adding concentrated hydrochloric acid to the filtrate under cooling and agitation. Then, 50 ml of methanol was added dropwise to the solution and the mixture was agitated at 5° C. overnight to effect crystallization. The precipitated crystal was recovered by filtration, washed with small amounts of cold water and cold ethanol and dried at room termperature under reduced pressure to obtain 420 mg (46% yield) of a crystal of 8-n-octylamino-c-AMP, properties of which were found to be as follows:

Decomposition Point: 223° C.

Ultraviolet Absorption Maximum: $\lambda_{max}^{pH2}$ 277 m$\mu$, $\lambda_{max}^{pH13}$ 277 m$\mu$, $\epsilon$hd $pH_2^{277}$ m$\mu$ 13,200, $E_{250}/E_{260}$ = 0.53, $E_{280}/E_{260}$ = 1.42

Paper Chromatography [n-butanol:acetic acid:water = 4:1:5 (upper layer)]: Rf value = 0.80

Elementary Analysis Values as $C_{18}H_{29}N_6O_6P$: Found: C = 46.29%, H = 6.52%, N = 18.20%, P = 6.53%.

Calculated: C = 47.36%, H = 6.40%, N = 18.42%, P = 6.78%.

EXAMPLE 16

To 60 ml of ethanol were added 820 mg (2 millimoles) of 8-bromo-c-AMP and 2.02 g (20 millimoles) of n-hexylamine, and the mixture was reacted at 100° C. for 6 hours in a glass bomb roll. The reaction mixture was post-treated in the same manner as described in Example 15, to obtain 497 mg (58% yield) of a crystal of 8-n-hexylamino-c-AMP, properties of which were found to be as follows:

Decomposition Point: 224° C.
Ultraviolet Absorption Maximum: $\lambda_{max}^{pH_2}$ 277 m$\mu$, $\lambda_{max}^{pH_{13}}$ 277 m$\mu$, $\epsilon_{pH_x}^{277\ m\mu}$ 13,600, $E_{250}/E_{260}$ = 0.52, $E_{280}/E_{260}$ = 1.45
Paper Chromatography [n-butanol:acetic acid:water = 4:1:5 (upper layer)]: Rf value = 0.78
Elementary Analysis Values as $C_{16}H_{25}N_6O_6P$: Found: C = 44.75%, H = 6.01%, N = 19.35%, P = 7.02%.
Calculated: C = 44.86%, H = 5.88%, N = 19.62%, P = 7.23%.

EXAMPLE 17

Procedures of Example 16 were repeated in the same manner except that 1.46 g (2 millimoles) of n-butylamine was used instead of 2.02 g of n-hexylamine, to obtain 520 mg (65% yield) of a crystal of 8-n-butylamino-c-AMP, properties of which were found to be as follows:

Decomposition Point: 223° C.
Ultraviolet Absorption Maximum: $\lambda_{max}^{pH_2}$ 277 m$\mu$, $\lambda_{max}^{pH_{13}}$ 277 m$\mu$, $\epsilon_{pH_2}^{277\ m\mu}$ 13,700, $E_{250}/E_{260}$ = 0.53, $E_{280}/E_{260}$ = 1.41
Paper Chromatography [n-butanol:acetic acid:water = 4:1:5 (upper layer)]: Rf value = 0.70
Elementary Analysis Values as $C_{14}H_{21}N_6O_6P$: Found: C = 41.80%, H = 5.35%, N = 21.22%, P = 7.68%.
Calculated: C = 42.00%, H = 5.29%, N = 21.00%, P = 7.74%.

EXAMPLE 18

To 40 ml of methanol were added 820 mg (2 millimoles) of 8-bromo-c-AMP and 2.36 g (40 millimoles) of n-propylamine, and the mixture was reacted at 80° C. for 5 hours in a glass ampoule. The resulting reaction mixture was post-treated in the same manner as described in Example 15, to obtain 540 mg (70% yield) of a crystal of 8-n-propylamino-c-AMP, properties of which were formed to be as follows:

Decomposition Point: 226° C.
Ultraviolet Absorption Maximum: $\lambda_{max}^{pH_2}$ 277 m$\mu$, $\lambda_{max}^{pH_{13}}$ 277 m$\mu$, $\epsilon_{pH_2}^{277\ m\mu}$ 13,400, $E_{250}/E_{260}$ = 0.49, $E_{280}/E_{260}$ = 1.45
Paper Chromatography [n-butanol:acetic acid:water = 4:1:5 (upper layer)]: Rf value = 0.56
Elementary Analysis Values as $C_{13}H_{19}N_6O_6P$: Found: C = 40.30%, H = 5.13%, N = 21.65%, P = 7.86%.
Calculated: C = 40.42%, H = 4.96%, N = 21.76%, P = 8.02%.

EXAMPLE 19

Procedures of Example 11 were repeated in the same manner except that 2.87 g (20 millimoles) of n-nonylamine was used instead of 3.14 g of n-decylamine, to obtain 706 mg (75% yield) of a crystal of 8-n-nonylamino-c-AMP, properties of which were found to be as follows:

Decomposition Point: 225° C.
Ultraviolet Absorption Maximum: $\lambda_{max}^{pH_2}$ 277 m$\mu$, $\lambda_{max}^{pH_{13}}$ 177 m$\mu$, $\epsilon_{pH_2}^{277\ m\mu}$ 13,000, $E_{250}/E_{260}$ = 0.60, $E_{280}/E_{260}$ = 1.37
Paper Chromatography [n-butanol:acetic acid:water = 4:1:5 (upper layer)]: Rf value = 0.75
Elementary Analysis Values as $C_{19}H_{31}N_6O_6P$: Found: C = 48.25%, H = 6.86%, N = 17.70%, P = 6.23%.
Calculated: C = 48.51%, H = 6.64%, N = 17.86%, P = 6.58%.

EXAMPLE 20

Procedures of Example 11 were repeated in the same manner except that 2.30 g (20 millimoles) of n-heptylamine was used instead of 3.14 g of n-decylamine, to obtain 549 mg (62% yield) of a crystal of 8-n-heptylamino-c-AMP, properties of which were found to be as follows:

Decomposition Point: 223° C.
Ultraviolet Absorption Maximum: $\lambda_{max}^{pH_2}$ 277 m$\mu$, $\lambda_{max}^{pH_{13}}$ 277 m$\mu$, $\epsilon_{pH_2}^{288\ m\mu}$ 13,400, $E_{250}/E_{260}$ = 0.52, $E_{280}/E_{260}$ = 1.42
Paper Chromatography [n-butanol:acetic acid:water = 4:1:5 (upper layer)]: Rf value = 0.72
Elementary Analysis Values as $C_{17}H_{27}N_6O_6P$: Found: C = 46.33%, H = 6.27%, N = 19.10%, P = 6.87%.
Calculated: C = 46.15%, H = 6.15%, N = 19.00%, P = 7.00%.

EXAMPLE 21

Procedures of Example 16 were repeated in the same manner except that 1.74 g (20 millimoles) of n-pentylamine was used instead of 2.02 g of n-hexylamine, to obtain 406 mg (49% yield) of a crystal of 8-n-pentylamino-c-AMP, properties of which were found to be as follows:

Decomposition Point: 223° C.
Ultraviolet Absorption Maximum: $\lambda_{max}^{pH_2}$ 277 m$\mu$, $\lambda_{max}^{pH_{13}}$ 277 m$\mu$, $\epsilon_{pH_2}^{277\ m\mu}$ 13,600, $E_{250}/E_{260}$ = 0.52, $E_{280}/E_{260}$ = 1.43
Paper Chromtography [n-butanol:acetic acid:water = 4:1:5 (upper layer)]: Rf value = 0.60
Elementary Analysis Values as $C_{15}H_{23}N_6O_6P$: Found: C = 43.60%, H = 5.78%, N = 20.10%, P = 7.32%.
Calculated: C = 43.48%, H = 5.60%, N = 20.28%, P = 7.48%.

What we claim is:
1. A cyclic adenosine monophosphate represented by the formula, or its pharmaceutically acceptable nontoxic inorganic or organic salt:

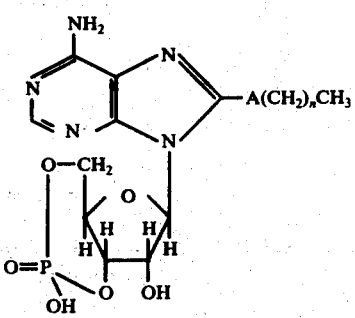

wherein A stands for —S— or —NH— and n is an integer of from 5 to 12.

2. An 8-alkylmercapto cyclic adenosine monophosphate according to claim 2, wherein A is —S—.

3. An 8-alkylmercapto cyclic adenosine monophosphate according to claim 2 wherein $n$ is an integer of from 5 to 8.

4. An 8-alkylmercapto cyclic adenosine monophosphate according to claim 2 wherein $n$ is an integer of from 9 to 12.

5. An 8-alkylamino cyclic adenosine monophosphate according to claim 1 wherein A is —NH—.

6. An 8-alkylamino cyclic adenosine monophosphate according to claim 5 wherein $n$ is an integer of 5 to 8.

7. An 8-alkylamino cyclic adenosine monophosphate according to claim 5 wherein $n$ is an integer of 9 to 12.

8. An 8-alkylmercapto cyclic adenosine monophosphate according to claim 2 wherein $n$ is 5.

9. An 8-alkylmercapto cyclic adenosine monophosphate according to claim 2 wherein $n$ is 6.

10. An 8-alkylmercapto cyclic adenosine monophosphate according to claim 2 wherein $n$ is 7.

11. An 8-alkylmercapto cyclic adenosine monophosphate according to claim 2 wherein $n$ is 8.

12. An 8-alkylmercapto cyclic adenosine monophosphate according to claim 2 wherein $n$ is 9.

13. An 8-alkylmercapto cyclic adenosine monohosphate according to claim 2 wherein $n$ is 10.

14. An 8-alkylmercapto cyclic adenosine monophosphate according to claim 2 wherein $n$ is 11.

15. An 8-alkylmercapto cyclic adenosine monophosphate according to claim 2 wherein $n$ is 12.

16. An 8-alkylamino cyclic adenosine monophosphate according to claim 5 wherein $n$ is 5.

17. An 8-alkylamino cyclic adenosine monophosphate according to claim 5 wherein $n$ is 6.

18. An 8-alkylamino cyclic adenosine monophosphate according to claim 5 wherein $n$ is 7.

19. An 8-alkylamino cyclic adenosine monophosphate according to claim 5 wherein $n$ is 8.

20. An 8-alkylamino cyclic adenosine monophosphate according to claim 5 wherein $n$ is 9.

21. An 8-alkylamino cyclic adenosine monophosphate according to claim 5 wherein $n$ is 10.

22. An 8-alkylamino cyclic adenosine monophosphate according to claim 5 wherein $n$ is 11.

23. An 8-alkylamino cyclic adenosine monophosphate according to claim 5 wherein $n$ is 12.

24. A pharmaceutical composition comprising an effective amount of a cyclic adenosine monophosphate or pharmaceutically acceptable non-toxic inorganic or organic salt thereof according to claim 1 and a pharmaceutically acceptable carrier therefor.

25. A pharmaceutical composition comprising an effective amount of a cyclic adenosine monophosphate or pharmaceutically acceptable non-toxic inorganic or organic salt thereof according to claim 2 and a pharmaceutically acceptable carrier therefor.

26. A pharmaceutical composition comprising an effective amount of a cyclic adenosine monophosphate or pharmaceutically acceptable non-toxic inorganic or organic salt thereof according to claim 3 and a pharmaceutically acceptable carrier therefor.

27. A pharmaceutical composition comprising an effective amount of a cyclic adenosine monophosphate or pharmaceutically acceptable non-toxic inorganic or organic salt thereof according to claim 4 and a pharmaceutically acceptable carrier therefor.

28. A pharmaceutical composition comprising an effective amount of a cyclic adenosine monophosphate or pharmaceutically acceptable non-toxic inorganic or organic salt thereof according to claim 5 and a pharmaceutically acceptable carrier therefor.

29. A pharmaceutical composition comprising an effective amount of a cyclic adenosine monophosphate or pharmaceutically acceptable non-toxic inorganic or organic salt thereof according to claim 6 and a pharmaceutically acceptable carrier therefor.

30. A pharmaceutical composition comprising an effective amount of a cyclic adenosine monophosphate or pharmaceutically acceptable non-toxic inorganic or organic salt thereof according to claim 7 and a pharmaceutically acceptable carrier therefor.

31. A method of treating diseases caused by disorder of the intracellular cyclic adenosine monophosphate level which comprises administering to a patient suffering from such disease an effective amount of a cyclic adenosine monophosphate or pharmaceutically acceptable non-toxic inorganic or organic salt thereof according to claim 1.

32. A method of treating diseases caused by disorder of the intracellular cyclic adenosine monophosphate level which comprises administering to a patient suffering from such disease an effective amount of a cyclic adenosine monophosphate or pharmaceutically acceptable non-toxic inorganic or organic salt thereof according to claim 2.

33. A method of treating diseases caused by disorder of the intracellular cyclic adenosine monophosphate level which comprises administering to a patient suffering from such disease an effective amount of a cyclic adenosine monophosphate or pharmaceutically acceptable non-toxic inorganic or organic salt thereof according to claim 3.

34. A method of treating diseases caused by disorder of the introcellular cyclic adenosine monophosphate level which comprises administering to a patient suffering from such disease an effective amount of a cyclic adenosine monophosphate or pharmaceutically acceptable non-toxic inorganic or organic salt thereof according to claim 4.

35. A method of treating diseases caused by disorder of the intracellular cyclic adenosine monophosphate level which comprises administering to a patient suffering from such disease an effective amount of a cyclic adenosine monophosphate or pharmaceutically acceptable non-toxic inorganic or organic salt thereof according to claim 5.

36. A method of treating diseases caused by disorder of the intracellular cyclic adenosine monophosphate level which comprises administering to a patient suffering from such disease an effective amount of a cyclic adenosine monophosphate or pharmaceutically acceptable non-toxic inorganic or organic salt thereof according to claim 6.

37. A method of treating diseases caused by disorder of the intracellular cyclic adenosine monophosphate level which comprises administering to a patient suffering from such disease an effective amount of a cyclic adenosine monophosphate or pharmaceutically acceptable non-toxic inorganic or organic salt thereof according to claim 7.

* * * * *

UNITED STATES PATENT AND TRADEMARK OFFICE
CERTIFICATE OF CORRECTION

PATENT NO. : 4,048,307  
DATED : September 13, 1977  
INVENTOR(S) : Takeshi Yokota, et al.

It is certified that error appears in the above-identified patent and that said Letters Patent are hereby corrected as shown below:

| | |
|---|---|
| Foreign Application Priority Data, Dec. 26, 1974 | cancel "49-3185" and substitute -- 50-3185 -- |
| Col. 1, line 67 | cancel "adenoisine" and substitute -- adenosine -- |
| Col. 2, line 9 | cancel "derivative" and substitute -- derivatives -- |
| Col. 2, line 54 | before "substituent" insert -- a -- |
| Col. 3, line 6 | cancel "8CH$_3$" and substitute -- 8-CH$_3$ -- |
| Col. 4, line 6 | cancel "epitherial" and substitute -- epithelial -- |
| Col. 5, last column | cancel "methylamino" and substitute -- Methylamino -- |
| Col. 7, line 53 | cancel "clincial" and substitute -- clinical -- |
| Col. 9, line 40 | cancel "n", 2nd occurrence, and substitute -- an -- |

UNITED STATES PATENT AND TRADEMARK OFFICE
CERTIFICATE OF CORRECTION

PATENT NO. : 4,048,307
DATED : September 13, 1977
INVENTOR(S) : Takeshi Yokota, et al.

It is certified that error appears in the above-identified patent and that said Letters Patent are hereby corrected as shown below:

| | |
|---|---|
| Col. 9, line 46 | cancel "sals" and substitute -- salts -- |
| Col. 16, line 58 | cancel "termperature" and substitute -- temperature -- |
| Col. 16, line 63 | cancel "Ehd" and substitute -- E -- |
| Col. 17, line 15 | cancel "$E_pH_x$" and substitute -- $E_pH_2$ -- |
| Col. 17, line 50 | cancel "formed" and substitute -- found -- |
| Col. 18, line 3 | cancel "177 mµ" and substitute -- 277 mµ -- |
| Col. 18, line 21 | cancel "$E_pH_22^{88}$" and substitute -- $E_pH_2 277$ -- |

UNITED STATES PATENT AND TRADEMARK OFFICE
CERTIFICATE OF CORRECTION

PATENT NO. : 4,048,307
DATED : September 13, 1977
INVENTOR(S) : Takeshi Yokota, et al.

It is certified that error appears in the above-identified patent and that said Letters Patent are hereby corrected as shown below:

Col. 18, line 68      cancel "claim 2" and substitute -- claim 1 --

Col. 19, line 23      cancel "monohosphate" and substitute -- monophosphate --

Col. 20, line 38      cancel "introcellular" and substitute -- intracellular --

Signed and Sealed this

Third Day of January 1978

[SEAL]

Attest:

RUTH C. MASON
*Attesting Officer*

LUTRELLE F. PARKER
*Acting Commissioner of Patents and Trademarks*